(12) United States Patent
Papay et al.

(10) Patent No.: US 11,351,377 B2
(45) Date of Patent: Jun. 7, 2022

(54) INTRA-ORAL APPLIANCES AND SYSTEMS

(71) Applicants: THE CLEVELAND CLINIC FOUNDATION, Cleveland, OH (US); XII Medical, Inc., Cleveland, OH (US)

(72) Inventors: Francis A. Papay, Westlake, OH (US); Kelly B. Emerton, Bay Village, OH (US); Charles P. Steiner, Pepper Pike, OH (US); Anthony V. Caparso, North Ridgeville, OH (US)

(73) Assignees: The Cleveland Clinic Foundation, Cleveland, OH (US); XII Medical, Inc., Cleveland, OH (US)

( * ) Notice: Subject to any disclaimer, the term of this patent is extended or adjusted under 35 U.S.C. 154(b) by 0 days.

(21) Appl. No.: 16/865,363

(22) Filed: May 3, 2020

(65) Prior Publication Data
US 2020/0346010 A1 Nov. 5, 2020

Related U.S. Application Data

(60) Provisional application No. 62/842,890, filed on May 3, 2019.

(51) Int. Cl.
| | |
|---|---|
| *A61N 1/36* | (2006.01) |
| *A61N 1/05* | (2006.01) |
| *A61N 1/372* | (2006.01) |
| *A61N 1/40* | (2006.01) |

(52) U.S. Cl.
CPC .......... *A61N 1/3611* (2013.01); *A61N 1/0548* (2013.01); *A61N 1/36078* (2013.01); *A61N 1/36128* (2013.01); *A61N 1/37252* (2013.01); *A61N 1/40* (2013.01)

(58) Field of Classification Search
CPC .......... A61N 1/0548; A61N 1/3611; A61N 1/36128; A61N 1/36078; A61N 1/37205; A61N 1/37252; A61N 1/3756; A61N 1/3787; A61N 1/40; A61F 5/56; A61F 5/566
USPC .......... 607/42
See application file for complete search history.

(56) References Cited

U.S. PATENT DOCUMENTS

| | | | |
|---|---|---|---|
| 2014/0135868 | A1 | 5/2014 | Bashyam |
| 2015/0290454 | A1* | 10/2015 | Tyler .......... G06F 3/012 607/134 |
| 2016/0106976 | A1 | 4/2016 | Kucklick |
| 2017/0143280 | A1 | 5/2017 | Kent et al. |
| 2017/0290699 | A1* | 10/2017 | Radmand .......... A61B 5/4557 |
| 2018/0015282 | A1* | 1/2018 | Waner .......... A61B 5/00 |

* cited by examiner

*Primary Examiner* — Carl H Layno
*Assistant Examiner* — Jane C Kalinock
(74) *Attorney, Agent, or Firm* — Levine Bagade Han LLP

(57) ABSTRACT

An intra-oral appliance to power and/or communicate with a neurostimulator is provided. The intra-oral appliance can include a teeth covering configured to fit over mandibular incisor, canine and/or premolar teeth of a human being and a remote controller in the form of a housing extending posteriorly from and operably connected to the teeth covering. The housing can include a power source, a coupling coil configured to transmit power to the neurostimulator and configured to receive power from an external charger, and electrical circuitry operably connected to the coupling coil and the power source.

17 Claims, 4 Drawing Sheets

INTRA-ORAL APPLIANCES AND SYSTEMS

CROSS-REFERENCE TO RELATED APPLICATIONS

The present application claims priority to U.S. Provisional Application No. 62/842,890, filed on May 3, 2019, the entirety of which is incorporated by reference herein.

TECHNICAL FIELD

An intra-oral appliance for powering and/or communicating with a neurostimulator is provided.

BACKGROUND

Preterm obstructive sleep apnea (OSA) is highly prevalent, affecting one in five adults in the United States. One in fifteen adults has moderate to severe OSA requiring treatment. Untreated OSA results in reduced quality of life measures and increased risk of disease including hypertension, stroke, heart disease, etc. Continuous positive airway pressure (CPAP) is a standard treatment for OSA. While CPAP is non-invasive and highly effective, it is not well tolerated by patients. Patient compliance for CPAP is often reported to be between 40% and 60%. Surgical treatment options for OSA, such as anterior tongue muscle repositioning, orthognathic bimaxillary advancement, uvula-palatal-pharyngoplasty, and tracheostomy are available too. However, they tend to be highly invasive (result in structural changes), irreversible, and have poor and/or inconsistent efficacy. Even the more effective surgical procedures are undesirable because they usually require multiple invasive and irreversible operations, they may alter a patient's appearance (e.g., maxillo-mandibulary advancement), and/or they may be socially stigmatic (e.g., tracheostomy) and involve extensive morbidity.

SUMMARY

Devices to power and/or communicate with a neurostimulator are provided herein. In an aspect, an energy delivery system is provided to activate and communicate with an indwelling neurostimulator placed proximate to a distal arborization of the hypoglossal nerve, within the genioglossus muscle, for example. An energy delivery system can include a removable intra-oral appliance that includes a remote controller for a neurostimulator. The energy coupling provides sufficient power to enable the neurostimulation device, using telemetric protocols, to modulate the delivery of a neurostimulation signal to a target site, such as, for example, the hypoglossal nerve. An intra-oral appliance can include a teeth covering configured to fit over mandibular incisor, canine and/or premolar teeth of a human being. The intra-oral appliance can also include a remote controller that is a hermetically sealed housing extending posteriorly from and operably connected to the teeth covering. The housing can comprise a power source, a coupling coil configured to transmit power to a neurostimulator and configured to receive power from an external charger, and a control circuit operably connected to the coupling coil and the power source. Neurostimulation systems are also provided that include an intra-oral appliance and a neurostimulator along with other components such as an external charger, a personal electronic device, and/or a programming device. Intra-oral appliances and systems including same can be used to improve sleep disordered breathing, including OSA, in patients suffering therefrom.

DETAILED DESCRIPTION

Devices for powering and/or communicating with neurostimulators are provided herein. The present disclosure refers to the term "substantially" with respect to certain shapes and configurations. By "substantially" is meant that the shape or configuration of the element need not have the mathematically exact described shape or configuration but can have a shape or configuration that is recognizable by one skilled in the art as generally or approximately having the described shape or configuration. The terms "anterior" and "posterior" are used herein with reference to a patient in a standard anatomical position. Further, as used herein with respect to a described element, the terms "a," "an," and "the" include at least one or more of the described element, including combinations thereof, unless otherwise indicated. Further, the term "or" refers to "and/or" and "combinations thereof" unless otherwise indicated. By "integral" or "integrated" is meant that the described components are fabricated as one piece or multiple pieces affixed during manufacturing or the described components are otherwise not separable using a normal amount of force without damaging the integrity (i.e. tearing) of either of the components. A normal amount of force is the amount of force a user would use to remove a component meant to be separated from another component without damaging either component. As used herein a "patient" includes a mammal such as a human being.

Figure 1:
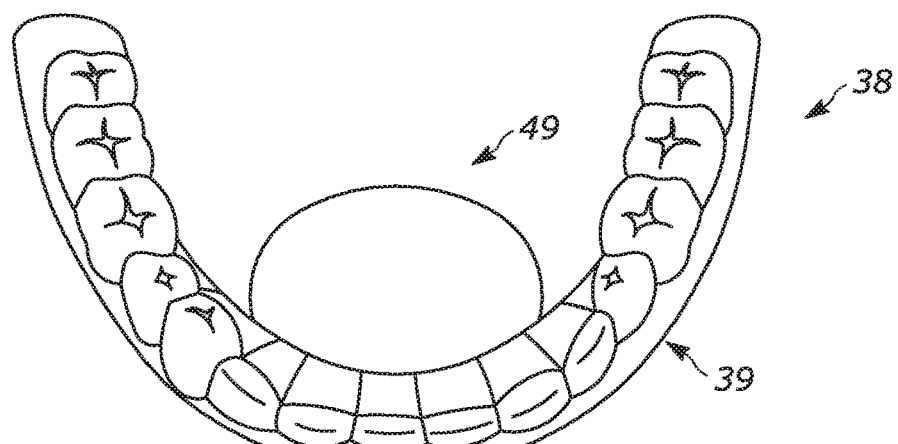
FIG. 1 is top view of an intra-oral appliance according to an aspect of the present disclosure.
Figure 2:
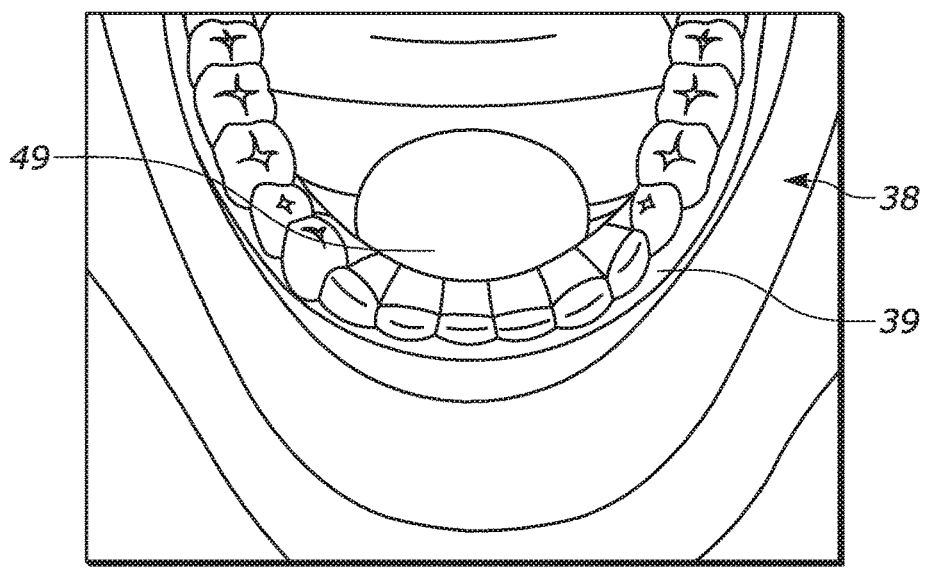
FIG. 2 is a top view of an intra-oral appliance positioned on a patient's teeth according to an aspect of the present disclosure.
Figure 3:
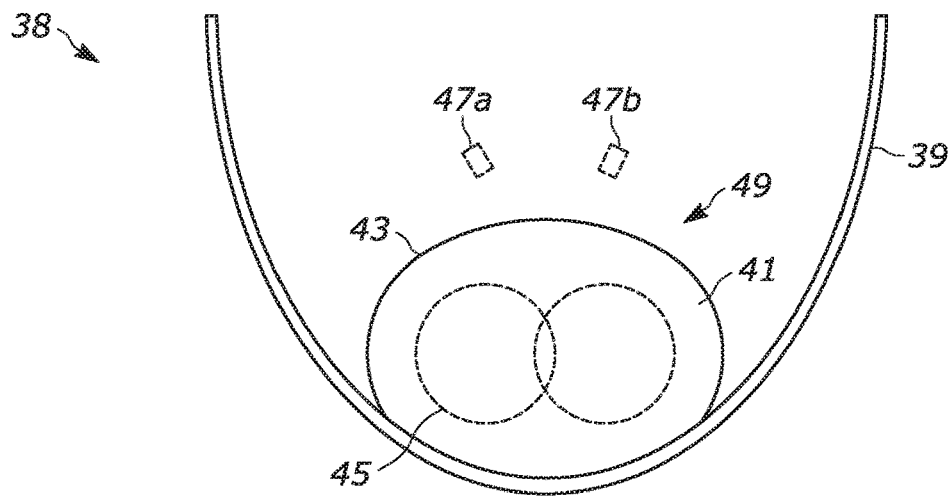
FIG. 3 is a top schematic view of an intra-oral appliance in spatial relation to implanted neurostimulators according to an aspect of the present disclosure.

An intra-oral appliance that includes a remote controller for powering and/or communicating with a neurostimulator is provided herein. Referring to FIGS. 1 to 3, intra-oral appliance 38 is configured to sit on the lower jaw or mandible of a patient suffering from sleep disordered breathing and temporarily affixes to the posterior surface of the teeth and rests underneath the tongue. In particular, intra-oral appliance 38 can comprise a mouthguard or teeth covering 39 having a substantially semi-circular shape configured to fit over a patient's mandibular incisor, canine and/or premolar teeth. Intra-oral appliance 38 can further include a remote controller 49 in the form of a housing 41 extending posteriorly from and operably connected to teeth covering 39 and configured to be positioned underneath the ventral surface of the tongue in an operable configuration (i.e. when therapy is ready to be initiated and the intra-oral appliance is worn by the patient). The teeth covering and housing can be an integral one-piece device. The housing can have a substantially ellipsoidal shape and can have a thickness of less than or equal to approximately five millimeters (mm) and an ellipsoidal diameter of less than or equal to three centimeters (cm). The geometry of intra-oral appliance naturally encourages the lower jaw to be positioned more anterior than normal thereby assisting with the opening of the patient's airway.

FIG. 2 is a schematic illustration of a top view of intra-oral appliance 38 depicting internal components of intra-oral appliance 38. Remote controller 49 can house a rechargeable or removable power source 43 and one or more coupling coils 45 arranged in a power/communication circuit such that power source 43 can provide electrical power for exciting coupling coils 45. Exciting coils 45 create a magnetic field that can reach one or more implanted neurostimulators 47. Neurostimulators 47 can include a coil and/or an antenna that is excited by the electromagnetic field generated by coupling coils 45, which induces a current in the neurostimulator coil/antenna. Through inductive coupling, the induced current can be used to power the implanted neurostimulators 47 for an extended period of time. For example, a rechargeable battery can provide as much as eight hours of power to a neurostimulator through this inductive coupling configuration.

It should be noted that neurostimulators 47 are individual components that are separate from the intra-oral appliance 38. FIG. 3 illustrates the relative spatial relationship between neurostimulators 47a and 47b and intra-oral appliance 38. The neurostimulators are implanted at a target site of neural or neuromuscular tissue, as described in more detail below. In the illustrated example configuration of the system, the intra-oral appliance 38 has no stimulating or sensing electrodes, as its purpose is to wirelessly power the implanted neurostimulators 47a and 47b through inductive coupling. However, the intra-oral appliance could have stimulating and/or sensing electrodes to stimulate tissue with the oral cavity and sense parameters within the oral cavity, such as tongue position, for example.

Figure 4:
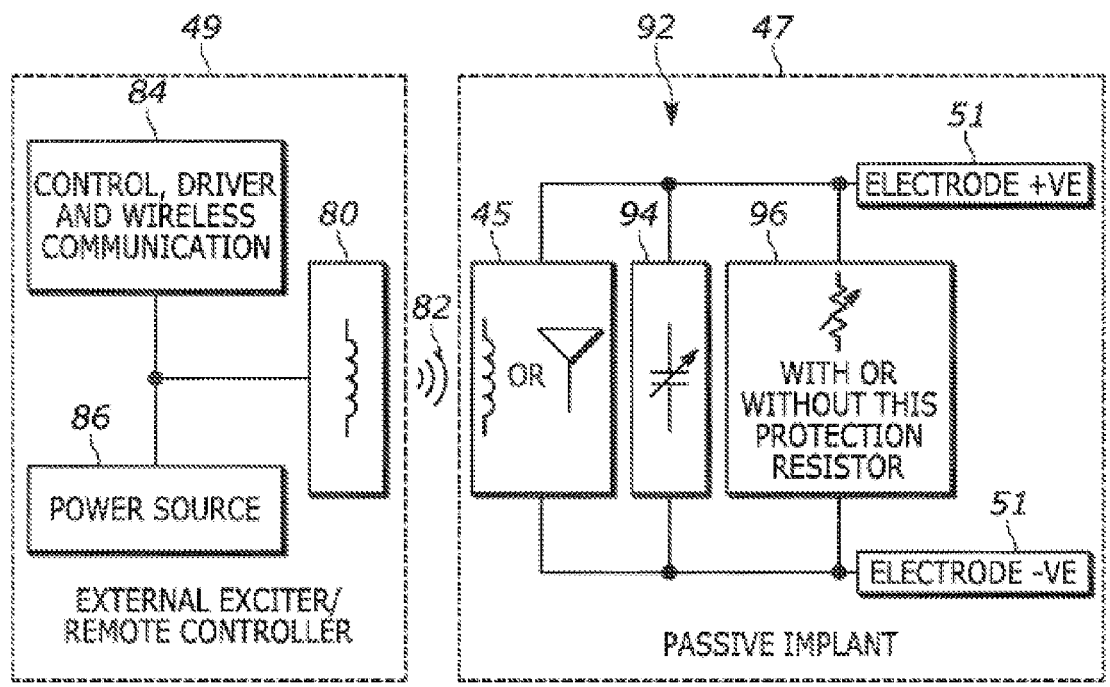
FIG. 4 is a block diagram illustrating components of a neurostimulator and a remote controller of an intra-oral appliance according to an aspect of the present disclosure.

Referring to FIG. 4, according to one aspect, neurostimulators 47 can be passive devices. By this, it is meant that the stimulation parameters with which neurostimulators 47 deliver electrical stimulation are determined by the current induced in the neurostimulators by remote controller 49. These stimulation parameters can, for example, include the amplitude, frequency, wavelength, waveform, pulse width, pulse phase, and polarity of the electrical stimulation signal. Remote controller 49 can include a control circuit 84, which includes, among other components, a microprocessor and memory used to store executable code, programming data, stimulation parameters, and other data, which the microprocessor uses to execute the control functions described herein. Control circuit 84 can be configured to utilize power source 86 to supply current to coupling coil 80 that displays signal characteristics defined by the desired stimulation parameters. The stimulation parameters can be programmed onto control circuit 84 via wireless communication, e.g., Bluetooth® or Wi-Fi® radio communication. This programming can be done through any Bluetooth enabled device, such as a smartphone, tablet computer, notebook computer, PC, etc. Other parameters, such as patient information, history, data logging, etc., can also be communicated in this manner.

Control circuit 84 can supply the current to the coupling coil with the desired signal characteristics, for example, through pulse-width modulation ("PWM"). Coupling coil 80, excited by this current, creates an electromagnetic field 82 that displays these same signal characteristics. Coils/antenna 45 of the neurostimulator are, in turn, excited by this field 82, which causes the current induced therein to have the same or substantially the same signal characteristics. Coils/antenna 45 form portions of a neurostimulator circuit 92 that includes a charge storage device 94, stimulation electrodes 51, and, optionally, a protection resistor/circuit 96. This induced current flows charges charge storage device 94 (e.g., a capacitor), which supplies electrodes 51. Electrodes 51 deliver the electrical stimulation with the signal characteristics of the induced current. It can thus be seen that, in this passive implementation of neurostimulator 47, the signal is passed through the device as received from remote controller 49.

In use, remote controller 49 can control neurostimulators 47 in an open loop control scheme, as described above. Alternatively, the neurostimulators can include sensors that provide feedback that can be relayed back to control circuit 84 for closed-loop control. Other devices, such as an external, wearable sensor or implantable sensor can be used to provide feedback. In one specific example, the sensors can be electrodes 51 or sensors implemented in neurostimulators 47. Remote controller 49 can apply stimulation via neurostimulators 47 according to stimulation program(s) stored in control circuit 84 memory. Stimulation programs can include predetermined, set programs (e.g., firmware) and adaptive, dynamic programs (e.g., software that is configurable/adaptable). The remote controller can select between various programs and/or actively modify a stimulation program according to various inputs received via Bluetooth® from a smartphone, tablet, etc. from a patient or doctor.

Figure 5:
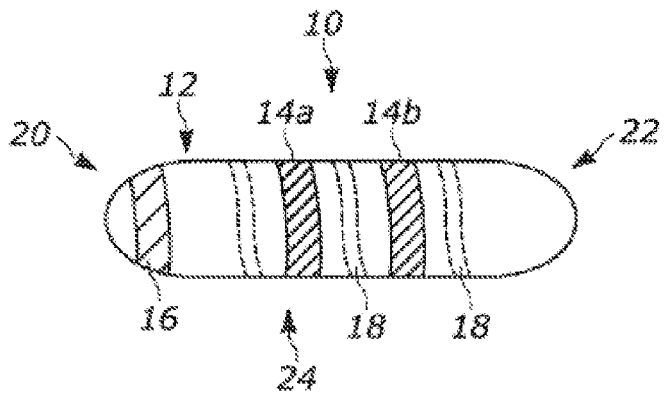
FIG. 5 is a side view of a neurostimulator according to an aspect of the present disclosure.

The neurostimulator that is powered and communicates with an intra-oral appliance as described herein can be an implantable neurostimulator such as an indwelling neurostimulator as described in U.S. Provisional Application No. 62/659,347 ("the '347 application"). The '347 application describes an injectable implant. Referring to FIG. 5, injectable implant 10 can comprise a body 12, at least one stimulating electrode 14a, 14b disposed on the body, and an antenna or coil 16 that is connected to the body for receiving power and/or stimulation parameters from a remote controller. Injectable implant 10 can also include a deployable fixation structure 18 that is housed within the body in a non-deployed configuration and, when actuated, forms a surface structure on the body that facilitates fixation in or about a target tissue. Body 12 can comprise a hermetically-sealed structure that has a generally tubular or cylindrical shape (e.g., isodiametric). In some instances, body 12 can have a hermetic integrity such that the leak rate is less than about $5 \times 10^{-8}$ atm cc/s He, and that moisture within the body through its service life is less than about 6000 ppm. Body 12 can include a proximal end portion 20, a distal end portion 22, and a middle portion 24 extending between the proximal and distal end portions. In one example, body 12 can have an outer diameter that is less than or equal to 5 mm and, for example, less than or equal to 2 mm. In another example, body 12 can have a length of about 50 mm or less, e.g., about 40 mm (e.g., about 30 mm), about 10 mm or 5 mm.

Figure 6:
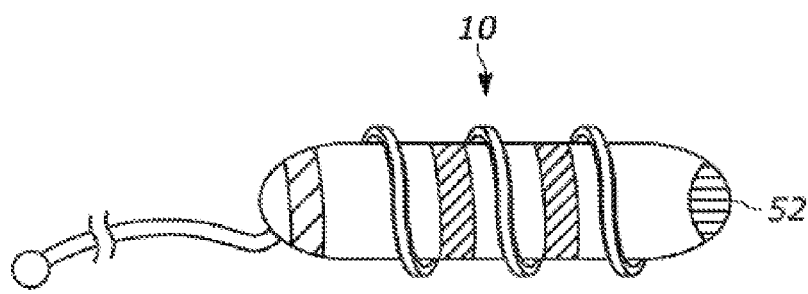
FIG. 6 is a side view of a neurostimulator according to an aspect of the present disclosure.
Figure 7:
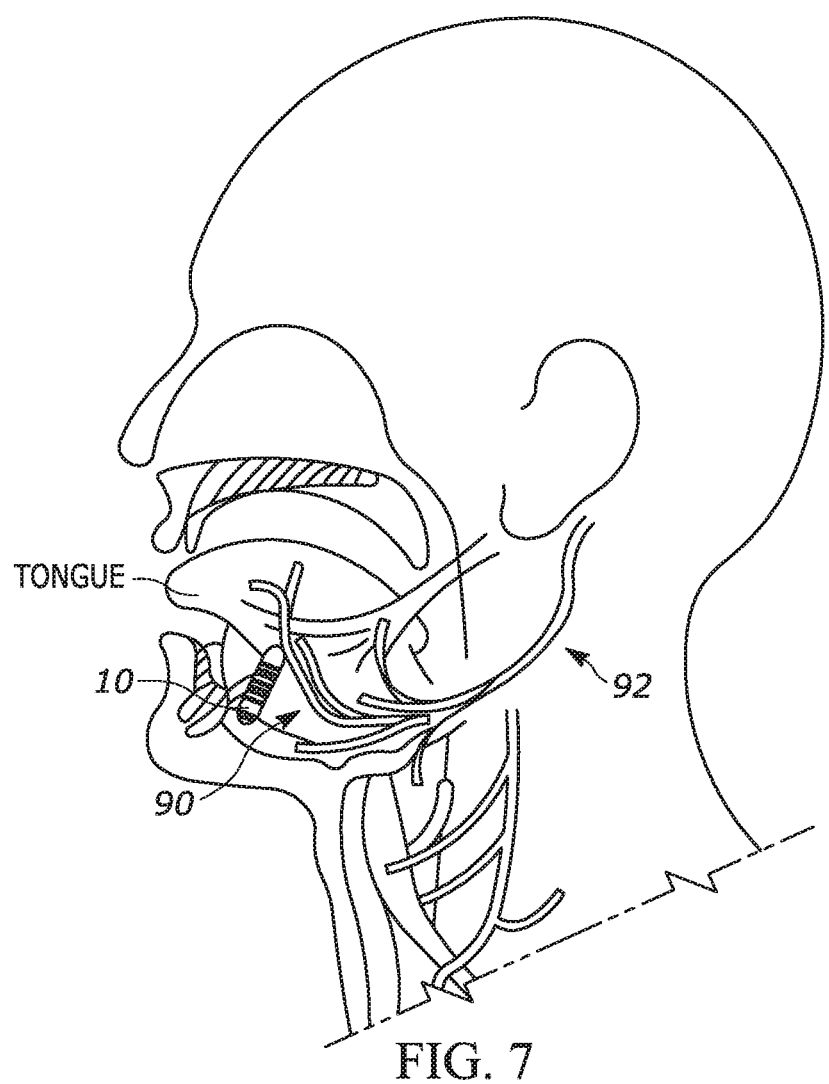
FIG. 7 is a schematic illustration of a neurostimulator implanted in a target site of a patient's body according to an aspect of the present disclosure.

As also shown in FIG. 6, implant 10 can include a sensor 52 to enable closed-loop operation of the implant. Sensor 52 can be disposed on body 12 and be configured or programmed to detect at least one physiological parameter, or a related symptom, associated with sleep disordered breathing, such as OSA. In one example, implant 10 can include an EMG sensor 52 that is capable of detecting the electrical activity produced by a muscle. Examples of muscles whose activity can be detected by an EMG sensor of the present disclosure are disclosed in U.S. Pat. No. 9,757,560 to Papay, which is incorporated by reference herein. In certain aspects, implant 10 can include an electrode capable of stimulation and sensing; in other words, a dual capacity electrode. The above-described neurostimulator is only exemplary and an intra-oral appliance can be used with other neurostimulators. In certain embodiments, the indwelling neurostimulator is positioned at a distal arborization 90 of the hypoglossal nerve 92 as illustrated in FIG. 7 (implant 10 enlarged for purposes of illustration).

Figure 8:
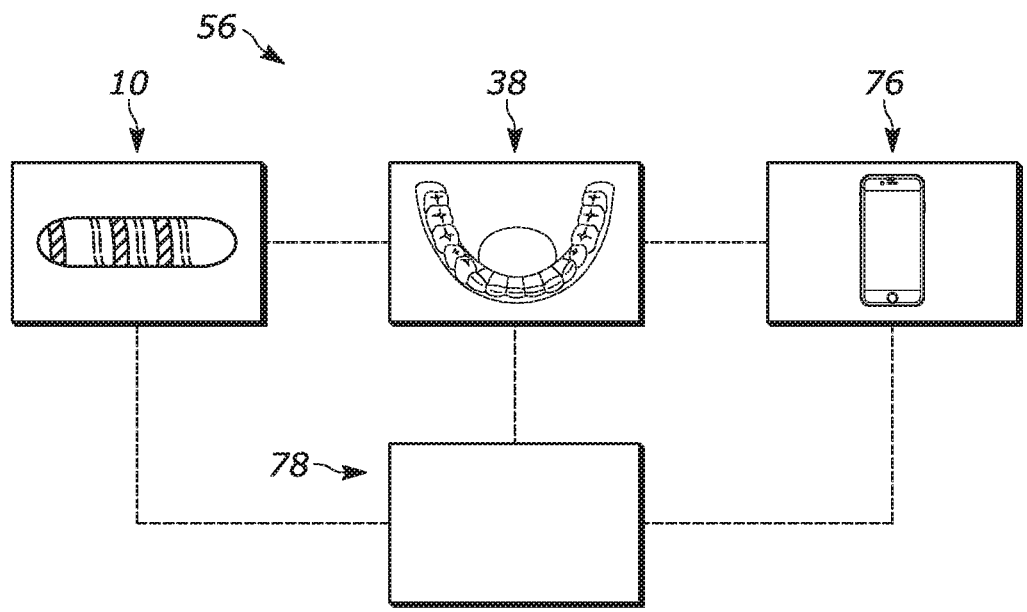
FIG. 8 is a block diagram of components of a neurostimulation system according to an aspect of the present disclosure.

Additional components of a neurostimulator system 56 are illustrated in FIG. 8 and can include intra-oral appliance 38, a personal electronic device 76, and a programming device 78. As shown in FIG. 8, neurostimulator 10 (which in FIG. 8 is illustrated as an injectable neurostimulator as described above but could have forms and configurations) can be in electrical communication (e.g., wireless communication) with intra-oral appliance 38 and programming device 78 (which is illustrated as a smartphone but could take other forms); the intra-oral appliance can be in electrical communication (e.g., wireless communication) with neurostimulator 10, the personal electronic device 76, and the programming device 78; the personal electronic device 76 can be in electrical communication (e.g., wireless communication) with the intra-oral appliance 38 and the programming device 76; and the programming device 78 can be in electrical communication (e.g., wireless communication) with the personal electronic device 76, the intra-oral appliance 38, and the neurostimulator 10.

All or only certain components of system 56 can be portable and adapted to be borne by a patient suffering from sleep disordered breathing for a desired period of time. In some instances, system 56 can be borne by a subject for an acute period of time (e.g., during an emergency situation), for a semi-chronic period of time (e.g., less than about a week to about 6 weeks), or for a chronic period of time (e.g., greater than about 6 weeks). For example, the neurostimulator can be temporarily or permanently implanted within, on, or otherwise associated with a subject suffering from sleep disordered breathing. The intra-oral appliance can be electrically coupled to an indwelling neurostimulator to deliver power and control signals to activate the neurostimulator, for example, during an eight hour treatment period, for sleep disordered breathing such as OSA.

Programming device 78 of system 56 can be configured and programmed to deliver stimulation and/or control instructions to the intra-oral appliance 38, and/or neurostimulator 10, and/or personal electronic device 76. In one example, programming device 78 can be configured as a dedicated, smart phone-sized unit. In another example, programming device 78 can be configured as a smart phone accessory dongle. In some instances, programming device 78 can be operated manually by the patient or a caregiver. In other instances, the programming device 78 can be battery powered and/or directly powered, e.g., by an AC source. If powered by rechargeable batteries, a battery charger may be an accessory to the programming device 78.

With respect to personal electronic device 76 of system 56, examples of personal electronic devices include smart phones and tablets; although, it will be appreciated that personal computers (PCs) may also be included. In some instances, the personal electronic device can include software programmed to control one or more stimulation and/or control parameters associated with the neurostimulator. Additionally, or optionally, the software comprising the personal electronic device can be programmed to store patient therapy data, such as diary questions and patient incentive information, and/or promote patient-to-patient interaction. The personal electronic device can also include software programmed to access remote data sources (e.g., Internet websites), query certain data, and then provide stimulation instructions to the system 56 based on the queried data. In another example, the personal electronic device can also include software programmed to provide the neurostimulator with customizable or patient-triggered alerts, e.g., indicating stimulation periods and the duration of each period, after a desired period of time after sleep onset, or after consumption of food or water. In some instances, the personal electronic device can be operated manually by the patient or a caregiver.

System 56 can be configured as an open-loop or closed-loop system. In an open-loop system, for example, a physician or the subject may, at any time, manually or by the use of pumps, motorized elements, etc., adjust treatment parameters of the system 56. Alternatively, in a closed-loop system (discussed below), treatment parameters (e.g., electrical signals) may be automatically adjusted in response to a sensed physiological parameter or a related symptom indicative of the extent of sleep disordered breathing, such as OSA. In a closed-loop feedback system, a sensor that senses a physiological parameter associated with sleep disordered breathing, such as OSA (e.g., muscle or nerve electrical activity, tongue position, oropharyngeal airflow, etc.) can be utilized. More detailed descriptions of sensors that may be employed in a closed-loop system, as well as other examples of sensors and feedback control techniques that may be employed as part of the present disclosure are disclosed in U.S. Pat. No. 5,716,377, which is incorporated by reference herein.

Figure 9:
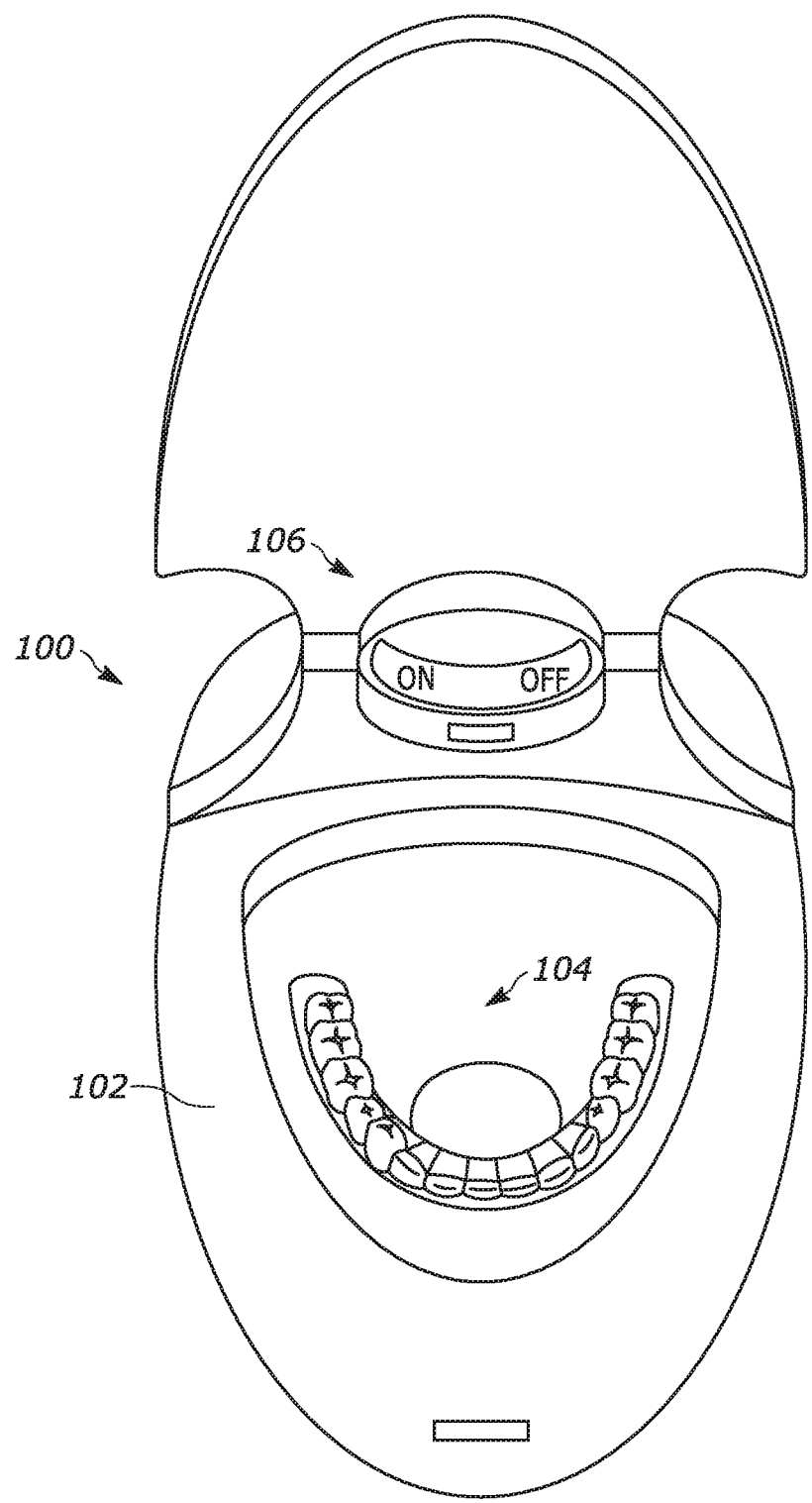
FIG. 9 is a perspective view of a re-charging device according to an aspect of the present disclosure.

Referring to FIG. 9, a neurostimulator system can include external recharging device 100 that incorporates wireless charging functionality by way of a wireless charging/coupling pad or coil incorporated into housing 102 of external recharging cradle 100 to re-charge an intra-oral appliance 104. Current from an internal or external power source can flow through the coil/pad inside recharging device 100, creating an electromagnetic field. Such an electromagnetic field can induce current in a coupling coil (e.g. inductive coupling) of intra-oral appliance 104 that is in electrical communication with the intra-oral appliance's battery. Such current can recharge the battery of the intra-oral appliance. As such, the external recharging device can provide wireless recharging of the remote controller of the intra-oral appliance. The external recharging device can also provide gentle ultrasonic or chemical cleaning of the teeth covering of the intra-oral appliance. The cleaning can be similar to other ultrasonic or chemical based cleaning system. The external recharging device can include a display 106 that indicates that the charging and cleaning function is either "off," "in progress" or "complete" by way of a multi-color indicator, for example. The wireless recharging function can provide a complete charge in 120 minutes using a 5V, 2A power source, for example.

Each of the disclosed aspects and embodiments of the present disclosure may be considered individually or in combination with other aspects and embodiments. Further, while certain features of embodiments may be shown in only certain figures, such features can be incorporated into other embodiments shown in other figures or otherwise disclosed in the specification. Additionally, when describing a range, all points within that range are included in this disclosure. In addition, unless otherwise specified, none of the steps of the methods of the present invention are confined to any particular order of performance.

What is claimed is:

1. An intra-oral appliance to treat sleep disordered breathing in a patient comprising:
   a teeth covering shaped in an arch and configured to fit over mandibular incisor, canine and/or premolar teeth of a human being;
   a remote controller comprising a substantially ellipsoidal housing extending posteriorly from a midline of the arch of the teeth covering and operably connected to the teeth covering, the remote controller sized and dimensioned to be positioned, in its entirety, in the intra-oral cavity and configured to be positioned underneath the ventral surface of the tongue in an operable configuration, the housing comprising:
   a power source;
   a coupling coil configured to transmit power to a neurostimulator and configured to receive power from an external charger; and
   a control circuit operably connected to the coupling coil and the power source.

2. The intra-oral appliance of claim 1, wherein the coupling coil is an induction coil.

3. A neurostimulator system comprising the intra-oral appliance of claim 1 and further comprising:
   the neurostimulator comprising a stimulating electrode and an antenna or coil configured to receive power and/or stimulation parameters from the remote controller.

4. The system of claim 3, further comprising the external charger comprising a charging coil configured to transmit power to the coupling coil of the remote controller, the coupling coil configured to charge the power source.

5. The system of claim 3, wherein the power source is a rechargeable battery.

6. The system of claim 3, further comprising a personal electronic device in communication with the remote controller, the personal electronic device including software to control one or more stimulation parameters associated with the neurostimulator.

7. The system of claim 6, further comprising a programming device configured to deliver stimulation instructions to the remote controller, the programming device being in communication with the remote controller and/or the personal electronic device.

8. The system of claim 3, wherein the system is configured to receive a sensed physiological parameter or a related symptom of sleep disordered breathing.

9. The system of claim 8, wherein the system is configured to automatically control one or more stimulation parameters in response to the sensed physiological parameter or related symptom.

10. The system of claim 3, wherein the neuro stimulator comprises an implant.

11. The system of claim 10, wherein the implant comprises:
    a body having a proximal end portion and a distal end portion;
    a stimulating electrode connected to the body; and
    an antenna or coil to receive power and/or stimulation parameters, wherein the antenna or coil is connected to the body.

12. The system of claim 11, further comprising at least one sensor attached to the body of the implant and configured to detect a physiological parameter or a related symptom of sleep disordered breathing.

13. The system of claim 10, further comprising a fixation structure that facilitates fixation of the body of the implant in or adjacent a target tissue.

14. The system of claim 13, wherein the fixation structure is deployable and is housed within the body of the implant in a non-deployed configuration and, when actuated, forms a surface structure on the body that facilitates fixation in or adjacent the target tissue.

15. The intra-oral appliance of claim 1, wherein the housing comprises a thickness of less than or equal to 5 mm.

16. The intra-oral appliance of claim 1, wherein the housing comprises the ellipsoidal diameter of less than or equal to 3 cm.

17. The intra-oral appliance of claim 1, wherein the teeth covering and the housing form an integral one-piece device.

* * * * *